United States Patent [19]

Welle et al.

[11] 4,081,551
[45] Mar. 28, 1978

[54] OXIME ETHERS HAVING ANTI-DEPRESSIVE ACTIVITY

[75] Inventors: Hendricus Bernardus Antonius Welle, Utrecht; Volkert Claassen, Weesp, both of Netherlands

[73] Assignee: U.S. Philips Corporation, New York, N.Y.

[21] Appl. No.: 668,490

[22] Filed: Mar. 19, 1976

[30] Foreign Application Priority Data

Mar. 20, 1975 Netherlands .................. 7503309

[51] Int. Cl.$^2$ ............ A61K 31/15; A61K 31/275; C07C 121/78; C07C 131/00
[52] U.S. Cl. .................. 424/304; 260/465 E; 260/501.19; 260/566 AE; 424/316; 424/327
[58] Field of Search .......... 260/566 AE, 465 E; 424/327, 304

[56] References Cited

U.S. PATENT DOCUMENTS 3,692,835  9/1972  Jan Van Dyk et al. ...... 260/566 AE

*Primary Examiner*—Dolph H. Torrence
*Attorney, Agent, or Firm*—Frank R. Trifari; Norman N. Spain

[57] ABSTRACT

A very powerful serotonine potentiation was found of oxime ethers of the formula

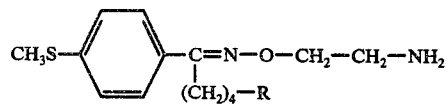

where R is methoxy, ethoxy, cyano, cyanomethyl, chlorine, methoxyethoxy or methoxymethyl and their salts which is associated with a much less strong noradrenaline potentiation. The compounds have no anti-depressive activity component based on monoamino oxidase inhibition and are substantially free from side effects.

10 Claims, No Drawings

OXIME ETHERS HAVING ANTI-DEPRESSIVE ACTIVITY

The invention relates to novel oxime ether compounds having anti-depressive activity.

British patent specification No. 1,205,665 describes a large group of compounds as having an anti-depressive, a sedative and/or an anticonvulsive activity. According to this patent specification, the anti-depressive activity of the known compounds is based on monoamino oxidase (MAO) inhibition and/or noradrenaline potentiation.

Compounds which inhibit MAO are particularly difficult to administer. They often have serious side effects and they are often incompatible with other medicines and nutrients. As the regulations governing the use of medicines become more and more stringent, only those compounds which are substantially free from noxious side effects can be considered for administration to human beings.

It is the object of the invention to provide novel anti-depressive compounds whose activity component is not based on monoamino oxidase inhibition and which in addition are substantially free from side effects and whose activity is primarily expressed in an elevation of the mood of the treated patient and to a much smaller extent in an increase of the motor activity.

Prior biochemical investigations in depressive patients, Brit. J. Psychiatr. 113 1407 (1967), Nature 225 1259 (1970), and Arch. Gen Psychiatr. 28 827 (1973) have lent support to the hypothesis that a decrease of the serotonergic processes in the brains is a factor in the pathogenesis of depressions.

Investigations in other patients, however, do not lead to this supposition (Arch. Gen. Psychiatr. 25 354 (1971)). Therefore, a current opinion, which is gaining support, is that there are classifications of patients whose several "sub-type" depressions are caused by different deviations in the metabolism of biogenic amines. This may explain why patients who fall into these different "sub-type" classifications of depression react differently to the treatment with anti-depressive compounds (Drugs 4, 361, (1972)).

The anti-depressive compounds now employed chemically influence the re-uptake of amines in the neurons to a different extent: desmethylimipramine and protriptyline have mainly a blocking effect on the cell membrane of noradrenergic neurons, while imipramine and amitriptyline also inhibit the re-uptake of senoromine by senotonergic neurons (J. Pharm. Pharmacol. 20 150 (1968), J. Pharmacol. 4 135 (1968)).

There are a number of brain processes in which serotonine and noradrenaline have opposite activities (Am. N.Y. Acad. Sci. 66 631 (1957), Adv. Pharmacol. 6B 97 (1968) and Jouvet in Van Praag: Brain and Sleep, 1974). In the medicinal treatment of depressive patients the intensification of the function of one amine might result in a decrease of the function of the other amine.

As shown above there exists a significant need for a compound useful as an anti-depressant whose activity consists mainly of a blocking of the cell membrane of the seroronergic neurons (Van Praag, Psyche aan banden, De Erven Bohn, B. V. Amsterdam, 1974), that is whose activity is mainly based on the potentiations of serotonine.

According to the invention it has been found that the novel compounds of formula I

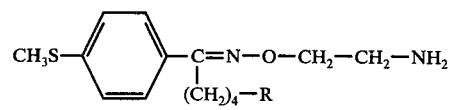

and salts thereof with pharmaceutically acceptable acids fulfil the requirements for an anti-depressive compound as set out above. These compounds show a very powerful serotonine potentiation which is associated with a weaker noradrenaline potentiation. These compounds do not have an activity component based on monoamino oxidase inhibition, ae substantially free from side effects, for example stomach ulceration and broncho-constriction, and have a very low toxicity.

In formula I, R has the following meaning: a methoxy group, an ethoxy group, a methoxyethoxy group, a methoxymethyl group, a cyano group or a cyanomethyl group or a chlorine atom.

While it is surprising that a very strong serotonine potentiation was found for the novel compounds of the invention, when compared with the compounds known from British patent specification No. 1,205,665 which known compounds only show an antidepressive activity based on noradrenaline potentiation and/or MAO inhibition even more surprising is the selectivity by which the compounds according to the invention potentiate serotonine (expressed in the low ratios $ED_{50}$ serotonine potentiation/$ED_{50}$ noradrenaline potentiation (serot.-/noradr.)).

The compounds according to the invention were compared with the most closely structurally related known compounds. The results of this investigation are recorded in the following table wherein the deffinition of R in each compound is given.

| Compound X | | noradr. pot. | serot. pot. | serot./ noradr. | MAO inhib. | stomach ulcer. | broncho constr. |
|---|---|---|---|---|---|---|---|
| $(CH_2)_4OCH_3$ | xx | 26 | 12 | 0.5 | >215 | — | — |
| $(CH_2)_4OC_2H_5$ | x | 36 | 20 | 0.2 | >215 | — | — |
| $(CH_2)_4OC_2H_4OCH_3$ | x | 45 | 34 | 0.8 | >215 | — | — |
| $(CH_2)_5OCH_3$ | xx | ~100 | 21 | ~0.2 | >215 | — | — |
| $(CH_2)_4CN$ | xx | 33 | 16 | 0.5 | >215 | — | — |
| $(CH_2)_5CN$ | xx | ~100 | 29 | ~0.3 | >215 | — | — |
| $(CH_2)_4Cl$ | x | >215 | 15 | <0.1 | >215 | — | — |
| $CH_3$ | xx | 2.4 | 0.74 | 0.3 | 15 | | — |
| $(CH_2)_4CH_3$ | xx | ~50 | 10 | ~0.2 | >215 | + | + | x = fumarate 1:1
xx = hydrochloride

In this table the ratios $ED_{50}$ denote values expressed in mg/kg. In the column serot./noradr. the ratio of the $ED_{50}$ values of the two preceding columns is recorded.

The selectivity of the compounds of the invention shown above the line relative to serotonine potentiation and furthermore the absence of undesired effects such as MAO inhibition, stomach ulceration and bronchoconstriction is clearly shown in this table.

Although the first of the known compounds which recorded below the dividing line also exhibits a powerful and a selective serotonine potentiation, this known compound does not satisfy the object of the invention since this compound also inhibits monoamino oxidase to a very considerable extent. The second known compound does not fulfil the abovementioned requirements since the compound causes both stomach ulceration and broncho-constriction.

In addition to the surprisingly powerful and selective serotonine potentiation, the absence of the said undesired side effects in the compounds according to the invention is unexpected, since these side effects are present in the structurally closely related compounds.

The results recorded in the table were obtained in the following tests.

The noradrenaline potentiation was determined in the tetrabenazine test. In this test a quantity of the compound to be tested was administered orally to five male albino mice. After 45 minutes the animals were injected subcutaneously with 80 mg/kg of tetrabenazine. After another 45 minutes the degree pf ptosis was determined and compared with the ptosis of animals which had received tetrabenazine alone. From the results the $ED_{50}$ was determined.

The serotonine potentiation was determined in the 5-hydroxytryptophan test. For this purpose the compounds to be tested were administered orally to isolated male albino mice in a series of dosages (5 mice per dosage) 1 hour prior to intraperitoneal administration of 150 mg/kg of dl-5-hydroxytryptophan. 30 Minutes after this threshold dosage the mice were observed individually and the following parameters were scored: stereotypical shaking of the head, spreading of the hindlegs, tremor, tendency to flee, lordosis, clonic stamping with the frontlegs. The $ED_{50}$-value as calculated from the results.

The monoamino oxidase (MAO) inhibiting activity was determined in experiments in which a quantity of the compound to be tested was administered orally to five male albino mice. One hour later the animals were injected subcutaneously with tryptamine hydrochloride in a quantity of 250 mg/kg. This quantity does not cause mortality in animals which do not receive the compound to be tested but does cause mortality in animals to which an active substance had been administered. Eighteen hours after the administration of tryptamine hydrochloride it was determined how many treated animals had died. The $ED_{50}$ was determined from the results obtained.

By means of the method by Metyšovà, Arzneimittelforschung 13 — 1039 (1963), it was determined whether the oral administration of 200 mg of a compound under test causes stomach ulceration. By means of the method of Konzett-Rössler, Arch. Exp. Path. Pharmakol. 195 71 (1940) it was investigated whether a compound under test causes broncho-constriction after intravenous administration of 3 mg of the compound. In this method reduction of the breathing function as a result of broncho-constriction is expressed in a smaller volume of air being taken in.

On the basis of their properties the compounds of formula I and their salts are particularly suitable for use in the treatment of depressive patients, in particular for mood elevation.

The quantity, the frequency and the route of administration of the substances may differ for each individual case, also in accordance with the severity of the disturbance to be treated. In general, a daily dose of 25–500 mg orally will be used for adults. As a rule a daily dose of 50–200 mg orally will suffice.

The compounds are preferably used in the form of pills, tablets, coated tablets, capsules, powders, injection liquids and the like. The compounds may be processed to form such compositions according to methods which are known per se.

The invention therefore also relates to compositions having a compound of formula I or a salt thereof as an active constituent with a pharmaceutically acceptable acid and to methods to prepare said compositions, for example, by mixing the active substance with or dissolving it in solid or liquid pharmaceutical carrier materials.

As examples of pharmaceutically acceptable acids with which compounds of formula I can form salts may be mentioned: inorganic acids, for example hydrochloric acid, sulphuric acid, nitric acid and organic acids, for example, citric acid, fumaric acid, tartaric acid, benzoic acid, maleic acid and the like.

The compounds of formula I and their salts may be prepared according to methods which are known for the preparation of this type of compounds and according to methods analogous thereto.

The invention also relates to the preparation of the compounds.

They can be obtained inter alia by converting a compound of formula II

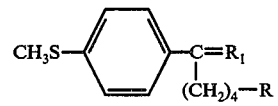

with the compound of formula III $H_2N-O-CH_2-CH_2-NH_2$ or a salt thereof. In formula II R has the same meaning as in formula I and $R_1$ is an oxygen atom, an oxime group or an alkylene dioxy group, for example ethylene dioxy. The reaction is preferably carried out in an inert solvent for example an alcohol, dioxan, dimethylformamide, tetrahydrofuran or a mixture thereof, at temperatures between room temperature and the boiling point of the mixture, and possibly in the presence of an acid binder, for example pyridine.

Another method consists of a reaction between a compound of formula IV

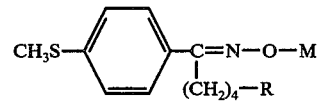

wherein M is a hydrogen atom or an alkali metal atom and R has the same meaning as in formula I and a compound of formula V $Hal-CH_2-CH_2-NH_2$ or a salt thereof wherein Hal is a halogen atom, preferably a chlorine atom or a bromine atom.

The reaction is preferably carried out in an inert solvent, for example alcohols, ethers, or dimethyl formamide. When M is a hydrogen atom, an acid binder is preferably added, for example an alcohol. As a rule the reaction temperature is between 0° and 50° C.

The compounds wherein R contains nitrogen or oxygen can also be obtained by reacting a compound of formula VI

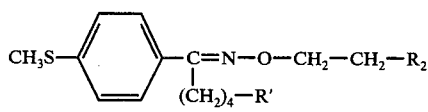

wherein R' is methoxy, ethoxy, methoxyethoxy, methoxymethyl, cyano or cyanomethyl and R₂ is a mesyloxy group or a tosyloxy group, with ammonia. The reaction is preferably carried out in an inert solvent, for example an alcohol, usually at temperatures between room temperature and 150° C.

The compounds of formula VI can be prepared by converting the corresponding compound of formula IV with ethylene oxide in ethanol and in the presence of an alcoholate at temperatures up to 60° C. The reaction product is then converted with tosylchloride or mesylchloride into a compound of formula VI preferably in an inert solvent, for example methylene chloride.

Another method of preparing the compounds of formula I wherein R contains nitrogen or oxygen consists of a reaction of a compound of formula VII

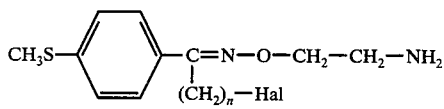

with a compound of formula VIII M'—R", in which formulae n has the value 4 or 5, Hal is a halogen atom preferably a chlorine atom or a bromine atom, M' is an alkali metal atom and R" is cyano, methoxy, ethoxy or methoxyethoxy.

This reaction is preferably carried out in an inert solvent, for example ethanol, dimethyl sulfoxide, dimethylformamide and the like, at temperatures between 0° and 70° C.

The compound of formula I wherein R contains an oxygen atom can also be obtained by converting a compound of formula IX

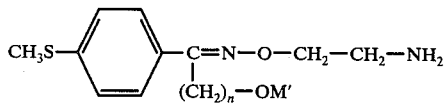

with a compound of formula X R₃—R'''. In these formulae M' is an alkali metal atom, R₃ is a halogen atom, for example a chlorine atom or a bromine atom, or a group (SO₄)½ and R''' is methyl, ethyl or methoxyethyl and n has the value 4 or 5.

The reaction is preferably carried out in an inert solvent, for example toluene or dimethylformamide. As a rule the reaction takes place at a temperature between 0° and 80° C.

The compounds of formula I wherein R contains an oxygen or chlorine can also be prepared by reducing a compound of formula XI

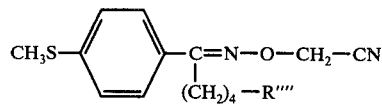

In this formula R'''' is methoxy, ethoxy, methoxyethoxy, methoxymethyl or chlorine, the reaction may be carried out with a reduction agent, for example a metal hydride, for example lithium aluminumtrimethoxy hydride, in a solvent, for example tetrahydrofuran, dioxan and the like at a temperature between 0° and 25° C.

The compounds of formula I can also be obtained by hydrolizing a compound of formula XII

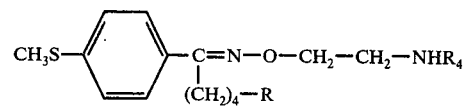

wherein R₄ is a protective group, for example a trityl group. The reaction may be carried out in an aqueous-inert solvent mixture, under acid conditions and at a temperature between room temperature and 100° C.

By diazotizing a compound of formula XIII

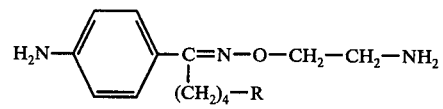

or a salt thereof with netrous acid and converting the reaction product with an alkali methylsulfide and copper, compounds of formula I can also be prepared. The diazation is carried out in a strong acid medium and the subsequent conversion reaction in a weak acid medium. As a rule the process temperature is between −10° and +5° C.

Another method of preparation consists of the methylation of a compound of formula XIV

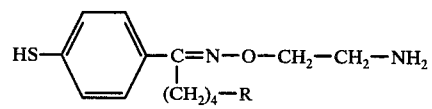

This reaction is carried out with a methylating agent, for example dimethyl sulfate, preferably in an inert solvent, for example water, in the presence of a base, for example NaOH.

The compounds of formula I wherein R contains an oxygen atom or a chlorine atom, can also be prepared by reducing a compound of formula XV

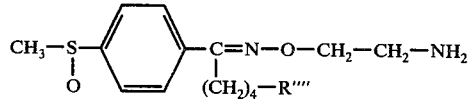

wherein R'''' has the same meaning as in formula XI.

A suitable reducing agent is, for example, a metal hydride, such as lithium aluminum trimethoxy hydride. The reaction is carried out in an inert solvent, for example, tetrahydrofuran, at a temperature between 0° and 25° C.

The invention will be described more detailed with reference to the following examples.

EXAMPLES

1. 5-Methoxy-4'-methylthiovalerophenone O-(2-aminoethyl) oxime hydrochloride 8 Mmol (1.9 g) of 5-methoxy-4'-methylthiovalerophenone (melting point 44°–45° C), 8.4 mmol (1.25 g) of 2-amino-oxyethylamine dihydrochloride and 4 ml of pyridine were refluxed for 2 hours in 8 ml of absolute ethanol. After evaporating the pyridine and the ethanol in vacuo, the residue was dissolved in water. The solution was washed with petroleum ether and 15 ml of 2N sodium hydroxide solution were then added. Three extractions with 40 ml of ether were than carried out. The ether extract was washed successively with 20 ml of 5% sodium bicarbonate solution and 20 ml of water. After drying on sodium sulfate the ether layer was evaporated in vacuo. Toluene was then evaporated three times (so as to remove the pyridine) and the resulting oil was dissolved in absolute ethanol. An equivalent quantity of 2N alcoholic hydrochlorid acid was added to this solution. The ethanol was then removed in vacuo and the residue was crystallized from ethanol/ether (1:4). The melting point of the resulting title compound was 112°–113.5° C.

2. 5-Ethoxy-4'-methylthiovalerophenone O-(2-aminoethyl) oxime furmarate (1:1)

The free base of the title compound was obtained in an identical manner from 5-ethoxy-4'methylthiovalerophenone (melting point 62°–63.5° C). The resulting oil was dissolved in absolute ethanol and an equimolar quantity of fumaric acid was added. Then there was heated until a bright solution was obtained and then there was crystallized at −5° C.

After sucking off and washing with cold ethanol there was dried in air. The resulting title compound has a melting point of 150°–151.5° C.

3. 5-(2-Methoxyethoxy)-4'-methylthiovalerophenone O-(2-aminoethyl) oxime furmarate (1:1)

6.3 Mmol (1.8 g) of 5-(2-methoxyethoxy)-4'-methylthiovalerophenone (melting point 39.5°–41.5° C), 6.3 mmol (0.94 g) of 2-aminoxyethylamine dihydrochloride and 1 ml of pyridine were refluxed for 3 hours in 6 ml of absolute ethanol. The processing was similar to example 1; after dissolving the resulting oil in 20 ml of absolute ethanol, an equimolar quantity of fumaric acid was added. There was then heated until a clear solution was obtained after which the ethanol was removed in vacuo. Crystallization from ethanol/ether yielded the title compound of melting point 137.5°–138.5° C.

4. 6-Methoxy-4'-methylthiocaprophenone O-(2-aminoethyl) oxime hydrochloride

25 Mmol (6.3 g) of 6-methoxy-4'-methylthiocaprophenone (melting point 53°–56° C), 25.5 mmol (3.8 g) of 2-amino-oxyethylamine dihydrochloride and 10 ml of pyridine were stirred for 3 days at room temperature together with 25 ml of absolute ethanol. The reaction product was then processed according to example 1 and converted into the hydrochloride salt. Crystallizations from successive quantities of benzene/petroleum ether (1:1) and acetonitrile yielded the title compound of melting point 86°–87.5° C.

5. 5-Cyano-4'-methylthiovalerophenone O'-(2-aminoethyl) oxime hydrochloride.

4.3 Mmol (1.0 g) of 5-cyano-4'-methylthiovalerophenone (melting point 81.5°–83° C), 4.3 mmol (0.35 g) of sodium acetate, 12 ml of ethanol and 1 ml of water were stirred at room temperature. Then 4.3 mmol (0.64 g) of 2-amino-oxyethylamine dihydrochloride were added and stirring was continued for 5 hours. The mixture was then partly evaporated in vacuo and diluted with water. Two extractions with ether were carried out and 4 ml of 50% sodium hydroxide solution were then added. Three extractions with $CH_2Cl_2$ were then carried out. The extract was washed successively with water, a 5% aqueous solution of sodium bicarbonate solution and with water. After drying on sodium sulfate the solution was evaporated in vacuo and toluene was evaporated three times. The resulting oil was dissolved in absolute ethanol. An equivalent quantity of 2N alcoholic hydrochloric acid was added to the solution. The ethanol was removed in vacuo and the residue was crystallized from ethanol/ether (1:3). The melting point of the resulting title compound was 129°–131° C.

6. 6-Cyano-4'-methylthiocaprophenone O-(2-aminoethyl) oxime hydrochloride

In the manner as described in Example 1 the title compound of melting point 113°–115.5° C was obtained from 6-cyano-4'-methylthiocaprophenone (melting point 49.5°–51° C).

7. 5-Chloro-4'-methylthiovalerophenone O-(2-aminoethyl) oxime fumarate (1:1)

In the manner as described in example 5 but with fumaric acid instead of hydrochloric acid, the title compound of melting point 149°–151° C was obtained from 5-chloro-4'-methylthiovalerophenone (melting point 87°–89° C).

8. 5-Cyano-4'-methylthiovalerophenone O-(2-aminoethyl) oxime hydrochloride 8.0 Mmol (4.2 g) of 5-cyano-4'methylthiovalerophenone O-(2-tritulaminoethyl) oxime were dissolved in 40 ml of 90% acetic acid. After leaving to stand at room temperature for 3 days this reaction mixture was evaporated to dryness in vacuo after which the residue was dissolved in 80 ml of ether. The solution was extracted with 40 ml of 0.2N hydrochloric acid and the extract, after rendering alkaline with 10 ml of 2N sodium hydroxide solution, was extracted with 50 ml and 25 ml of methylene chloride. The resulting solution was dried (sodium sulfate) and evaporated in vacuo. The residue was dissolved in 70 ml of absolute ethanol and converted into the title compound of melting point 129°–131° C by the addition of ethanolic hydrochloric acid.

9. 5-Methoxy-4'-methylthiovalerophenone O-(2-aminoethyl) oxime hydrochloride 5.0 Mmol (1.26 g) of 5-methoxy-4'-methylthiovalerophenone oxime (melting point 67.5°–69° C), 5.3 mmol (0.60 g) of 2-chloroethylamine hydrochloride and 0.7 g of KOH powder were added, while stirring at 10° C, to 12.5 ml of dimethylformamide (DMF). After stirring at room temperature for 2 days the DMF was removed in vacuo, the residue was brought in water and 2N hydrochloric acid was then added until $pH \times 3$. The remaining oxime was removed by means of ether after which 15 ml of 2 N sodium hydroxide solution were added. Three extractions with ether were then carried out. The collected ether layers were washed with a 5% sodium bicarbonate solution and dried on sodium sulphate. After removing the ether in vacuo the residue was taken up in absolute ethanol and acidified with ethanolic hydrochloric acid. The title compound obtained in this manner had a melting point of 112°–113.5° C.

10. 5-(2-methoxyethoxy)-4'-methylthiovalerophenone O-(2-aminoethyl) oxime fumarate (1:1)

7 Mmol (2.3 g) of 5-(2-methoxyethoxy)-4'-methylthiovalerophenone ethylene ketal and 7 mmol (1.0 g) of 2-amino-oxy-ethylamine dihydrochloride were refluxed for 4 hours in 10 ml of methanol. The methanol was evaporated in vacuo and the residue was dissolved in water followed by two washings with ether. 3 ml of 50% sodium hydroxide solution were then added and three extractions with $CH_2Cl_2$ were carried out. The extract was washed with 5% sodium bicarbonate solution and with water. The solution was then dried on sodium sulfate and the $CH_2Cl_2$ was distilled off in vacuo. The residue was dissolved in the usual manner in absolute ethanol and an equimolar quantity of fumaric acid and was added. The solvent was evaporated. After crystallisation from ethanol/ether (1:1) the title compound of melting point 136.5°–138.5° C was obtained.

11. 5-Ethoxy-4'-methylthiovalerophenone O-(2-aminoethyl) oxime fumarate (1:1)

In an identical manner the title compound having a melting point of 149°–151° C was obtained from 5-ethoxy-4'-methylthiovalerophenone ethylene ketal.

12. 6-Methoxy-4'-methylthiocaprophenone O-(2-aminoethyl) oxime hydrochloride 45 Mmol (12.5 g) of 4'-amino-6-methoxycaprophenone O-(2-aminoethyl) oxime were suspended in 120 ml of 2.7N sulfuric acid and, after heating to partial solution, the suspension was rapidly cooled to 0° C. A solution of 45 mmol (3.1 g) of $NaNO_2$ in 30 ml of water was then added at 0° C. Stirring at 0° C was then continued for 15 minutes and while cooling with ice 645 mmol (52.9 g) of sodium acetate were added scoop-wise at +5° C. This mixture was added dropwise in 1 hour while stirring at 0° C to a solution of 65.5 mmol (4.6 g) of methanethiol in 45 ml of 7.7N sodium hydroxide solution to which 18.9 mgat (1.2 g) of copper powder had been added. Stirring at 0° C was then continued for another 30 minutes and dilute sodium hydroxide solution was added until a strongly basic medium had been obtained. 3 Extractions with $CH_2Cl_2$ was distilled off in vacuo. The residue was purified chromatographically over silica gel with ethanol/ammonia (95:5) as an eluent. The solvents were distilled off in vacuo. The residue was taken up in absolute ethanol. An equimolar quantity of alcoholic hydrochloric acid was added to the mixture. After a clear solution had been obtained, the alcohol was evaporated. After crystallisation from acetonitrile the title compound of melting point 86°–87° C was obtained.

13. 5-Chloro-4'-methylthiovalerophenone O-(2-aminoethyl) oxime fumarate (1:1)

The title compound of melting point 148°–151° C was obtained in an identical manner but by the addition of fumaric acid from 4'-amino-5-chlorovalerophenone O-(2-aminoethyl) oxime.

14. 6-Cyano-4'-methylthiocaprophenone O-(2-aminoethyl) oxime hydrochloride

10 Mmol (3.1 g) of 6-chloro-4'-methylthiocaprophenone O-(2-aminoethyl)oxime were dissolved in 10 ml of dimethyl-sulfoxide (DMSO) and 25 mmol (1.2 g) of sodium cyanide were then added. This suspension was heated at a temperature of 50° to 70° C for 4 hours and then cooled to room temperature. The suspension was then diluted 2ith 100 ml of 0.5N sodium hydroxide solution and extracted three times with 40 ml of ether. The ether extract was washed with water, dried on sodium sulfate and evaporated in vacuo. The residue was purified chromatographically over silica gel with ethanol/ammonia (95:5) as an eluent. After evaporating the solvents the hydrochloride of the resulting substance was prepared by dissolving in ethanol and acidifying with alcoholic hydrochloric acid. After crystallisation from ethanol/ether (1:4) the title compound having a melting point of 114°–115.5° C was obtained.

15. 5-Ethoxy-4'-methylthiovalerophenone O-(2-aminoethyl) oxime fumarate (1:1)

12 Mmol (5.0 g) of 5-chloro-4'-methylthiovalerophenone O-(2-aminoethyl) oxime fumarate (1:1) (melting point 149°–151° C) were added to a solution of 249 mgat (5.5 g) of sodium in 100 ml of absolute ethanol followed by heating at 70° C for 8 hours. The mixture was then neutralised at 0° C with alcoholic hydrochloric acid and the sodium chloride was filtered off. The alcohol was distilled off in vacuo and the residue was dissolved in water. 5 ml of 50% sodium hydroxide solution were added to said solution after which three extractions were carried out with 40 ml of ether. The ether extract was washed with 5% sodium bicarbonate solution and with water and dried on sodium sulfate. The residual ether was distilled off in vacuo and the residue was dissolved in ethanol after which an equimolar quantity of fumaric acid was added. After crystallization from ethanol the title compound was obtained having a melting point of 149°–151.5° C.

16. 5-Methoxy-4'-methylthiovalerophenone O-(2-aminoethyl) oxime. HCl (a) 26 Mmol (1.15 g) of ethylene oxide were led by means of a flow of nitrogen into a suspension of 15.5 mmol of 5-methoxy-4'-methylthiovalerophenone oxime (melting point 67.5°–69° C) in 25 ml of absolute ethanol in which 0.03 g of Li had first been dissolved, while stirring and at 55° C, followed by stirring for another hour at 60° C. After the addition of 0.3 ml of acetic acid, the ethanol was distilled off in vacuo. The residue was purified chromatographically by means of silica gel and with $CH_2Cl_2$ as an eluent. After evaporating the solvent the O-(2-hydroxyethyl) oxime was obtained as an oil.

(b) To a solution of 11 mmol hereof in 70 ml of methylene chloride were added while stirring at −5° to 0° C 2.25 ml of triethylamine and then 12 mmol (0.9 ml) of mesylchloride were added dropwise in approximately 20 minutes. Stirring was continued for 30 minutes at 0° C, the mixture was then washed successively with ice-water (4×), a 5% sodium bicarbonate solution of 0° C and a saturated NaCl solution of 0° C (2×). After drying on sodium sulfate at 5° C, the $CH_2Cl_2$ was distilled off in vacuo at a bath temperature of 40° to 60° C. The O-(2-mesyloxyethyl) oxime was obtained in this manner.

(c) A mixture of 8 mmol hereof in 30 ml of methanol which contained 245 mmol (4.2 g) of NH₃ was kept in an autoclave at 100° C for 14 hours. After cooling the methanol was removed in vacuo, the residue was stirred with 50 ml of 2N sodium hydroxide solution and extracted with ether. The collected ether extracts were washed with a 5% sodium bicarbonate solution. After drying on sodium sulfate and distilling off the ether in vacuo the residue was dissolved in absolute ethanol. An equimolar quantity of ethanolic hydrochloric acid was added. After a clear solution had been obtained, the alcohol was evaporated. The residue was taken up in ethanol/ether (1:4). The title compound with a melting point of 111.5°–113.5° C was obtained.

17. 5-(2-Methoxyethoxy-4'-methylthiovalerophenone O-(2-aminoethyl) oxime fumarate (1:1)

24.7 Mmol (1.00 ml) of methanol in 3 ml of tetrahydrofuran (THF) were added while stirring and cooling in ice-water and within 3 minutes to 7.8 mmol (0.3 g) of LiAlH₄ in 10 ml of THF. While stirring and cooling and within 10 minutes a solution of 1.15 mmol (0.39 g) of 5-(2-methoxyethoxy)-4'-methylthiovalerophenone O-(cyanomethyl) oxime was added. After stirring the reaction mixture for another 3.5 hours at +5° C it was decomposed with 1.0 ml of water. The formed hydroxides were sucked off and washed with chloroform. The filtrate was evaporated to dryness in vacuo. The resulting base was dissolved in absolute ethanol and converted into the title compound by the addition of an equimolar quantity of fumaric acid. The melting point after recrystallisation from ethanol/ether (1:1) was 137°–138.5° C.

18. 6-Methoxy-4'-methylthiocaprophenone O-(2-aminoethyl) oxime hydrochloride In an identical manner but by using hydrochloric acid instead of fumaric acid, the title compound with a melting point 86°–87° C was obtained from 6-methoxy-4'-methylthiocaprophenone O-(cyanomethyl) oxime.

19. 5-Methoxy-4'-methylthiovalerophenone O-(2-aminoethyl) oxime hydrochloride (a) 0.68 Mmol (0.29 g) of 5-methoxy-4'-methylsulfinylvalerophenone O-(2-aminoethyl) oxime fumarate (1:1) (melting point 101°–105° C) was dissolved in 20 ml of water and 5 ml of 2N sodium hydroxide solution was added, extraction with 5×10 ml of CCl₃H was then carried out and after drying on sodium sulfate the extract was evaporated to dryness in vacuo. The resulting 0.67 mmol (0.21 g) of 5-methoxy-4'-methylsulfinylvalerophenone O-(2-aminoethyl) oxime was dissolved in 5 ml of tetrahydrofuran (THF).

(b) 24.7 Mmol (1.0 ml) of methanol in 3 ml of THF were added within 3 minutes to 7.8 mmol (0.3 g) of LiAlH₄ in 10 ml of THF while stirring and cooling in ice-water. While stirring and cooling continued and within a further 10 minutes the solution of 0.68 mmol (0.21 g) of 5-methoxy-4'-methylsulfinylvalerophenone O-(2-aminoethyl) oxime was then added. After stirring the reaction mixture at +5° C for another 3 hours it was decomposed with 1.0 ml of water. The formed hydroxides were sucked off, washed with chloroform and the filtrate was evaporated to dryness in vacuo. The resulting based was dissolved in ethanol. The solution was acidified with ethanolic hydrochloric acid. After recrystallization from ethanol/ether (1:1) the melting point was 112°–113° C.

20. 5-Chloro-4'-methylthiovalerophenone O-(2-aminoethyl) oxime fumarate (1:1)

In an identical manner but by using fumaric acid instead of hydrochloric acid, the title compound with a melting point of 148°–151° C was obtained from 5-chloro-4'-methylsulfinylvalerophenone O (2-aminoethyl) oxime fumarate (1:1) (melting point 123°–126° C.

21. Tablet 50 mg of 5-methoxy-4'-methylthiovalerophenone O-(2-aminoethyl) oxime HCl
335 mg of lactose
60 mg of potato starch
25 mg of talc
5 mg of magnesium stearate
5 mg of gelatin.

22. Suppository 50 mg of 6-methoxy-4'-methylthiocaprophenone O-(2-aminoethyl) oxime HCl
1500 mg of suppository mass

23. Injection liquid 25 mg of 5-methoxy-4'-methylthiovalerophenone O-(2-aminoethyl)oxime HCl
1.80 of methyl p-hydroxybenzoate
0.20 g of propyl p-hydroxybenzoate
9.0 g of sodium chloride
4.0 g of poly(oxyethylene)₂₀ sorbitan monooleate water to 1000 ml.

What is claimed is:

1. Oxime ether compounds of the formula

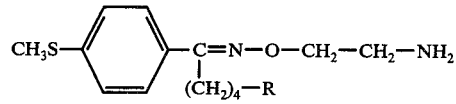

and salts thereof with pharmaceutically acceptable acids, in which formula R is methoxy, ethoxy, methoxyethoxy, methoxymethyl, cyano cyanomethyl or chlorine.

2. The 5-Methoxy-4'-methylthiovalerophenone O-(2-aminoethyl) oxime and salts thereof with pharmaceutically acceptable acids of claim 1.

3. The 5-Ethoxy-4'-methylthiovalerophenone O-(2-aminoethyl) oxime and salts thereof with pharmaceutically acceptable acids of claim 1.

4. The 5-(2-Methoxyethoxy)-4'-methylthiovalerophenone O-(2-aminoethyl) oxime and salts thereof with pharmaceutically acceptable acids of claim 1.

5. The 6-Methoxy-4'-methylthiocaprophenone O-(2-aminoethyl) oxime and salts thereof with pharmaceutically acceptable acids of claim 1.

6. The 5-Cyano-4'-methylthiovalerophenone O-(2-aminoethyl) oxime and salts thereof with pharmaceutically acceptable acids of claim 1.

7. The 6-Cyano-4'-methylthiocaprophenone O-(2-aminoethyl) oxime and salts thereof with pharmaceutically acceptable acids of claim 1.

8. The 5-Chloro-4'-methylthiovalerophenone O-(2-aminoethyl) oxime and salts thereof with pharmaceutically acceptable acids of claim 1.

9. A method of treating depressed patients, administering to said patients an antidepressively effective quantity of a compound of the formula

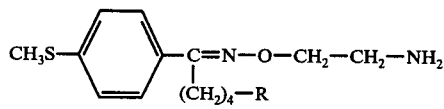

wherein R is ethoxy, methoxy, methoxyethoxy, methoxymethyl, cyano, cyanomethyl or chlorine or a salt thereof with a pharmaceutically acceptable acid 10. An antidepressive composition comprising an antidepressively content of a compound of the formula

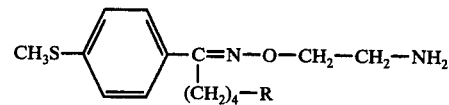

wherein R is ethoxy, methoxy, methoxyethoxy, methoxymethyl, cyano, cyanomethyl or chlorine or a salt thereof with a pharmaceutically acceptable acid and a pharmaceutically acceptable carrier therefor.

* * * * *

UNITED STATES PATENT AND TRADEMARK OFFICE
CERTIFICATE OF CORRECTION

PATENT NO. : 4,081,551
DATED : March 28, 1978
INVENTOR(S) : HENDRICUS BERNARDUS ANTONIUS WELLE ET AL It is certified that error appears in the above-identified patent and that said Letters Patent are hereby corrected as shown below:

Column 2, line 27, "ae" should be -- are --.

line 47, "deffinition" should be -- definition --.

in the heading of the table, "Compound X" should be

-- R --.

Signed and Sealed this

Twenty-second Day of August 1978

[SEAL]

Attest:

RUTH C. MASON
Attesting Officer

DONALD W. BANNER
Commissioner of Patents and Trademarks